(12) United States Patent
Iddan

(10) Patent No.: US 7,901,366 B2
(45) Date of Patent: Mar. 8, 2011

(54) SYSTEM AND METHOD FOR DETERMINING IN VIVO BODY LUMEN CONDITIONS

(75) Inventor: Gavriel J. Iddan, Haifa (IL)

(73) Assignee: Given Imaging, Ltd., Yoqneam (IL)

( * ) Notice: Subject to any disclaimer, the term of this patent is extended or adjusted under 35 U.S.C. 154(b) by 0 days.

(21) Appl. No.: 12/275,503

(22) Filed: Nov. 21, 2008

(65) Prior Publication Data

US 2009/0076370 A1 Mar. 19, 2009

Related U.S. Application Data

(62) Division of application No. 10/046,540, filed on Jan. 16, 2002, now Pat. No. 7,468,044.

(60) Provisional application No. 60/261,189, filed on Jan. 16, 2001.

(51) Int. Cl.
*A61B 5/00* (2006.01)
*A61B 1/06* (2006.01)
*B65D 81/00* (2006.01)

(52) U.S. Cl. .................................. 600/584; 600/160

(58) Field of Classification Search .............. 600/117, 600/118, 160, 310, 343, 473, 476, 562, 573, 600/575, 582, 584, 587, 593; 128/903
See application file for complete search history.

(56) References Cited

U.S. PATENT DOCUMENTS

| | | | |
|---|---|---|---|
| 3,683,389 A | 8/1972 | Hollis | |
| 3,971,362 A | 7/1976 | Pope et al. | |
| 4,038,485 A | 7/1977 | Johnston et al. | |
| 4,239,040 A | 12/1980 | Hosoya et al. | |
| 4,278,077 A | 7/1981 | Mizumoto | |
| 4,306,877 A | 12/1981 | Lubbers | |
| 4,439,197 A | 3/1984 | Honda et al. | |
| 4,689,621 A | 8/1987 | Kleinberg | |
| 4,741,327 A | 5/1988 | Yabe | |
| 4,817,632 A | 4/1989 | Schramm | |
| 4,844,076 A | 7/1989 | Lesho et al. | |
| 4,936,823 A | 6/1990 | Colvin et al. | |
| 5,006,314 A | 4/1991 | Gourley et al. | |
| 5,088,492 A | 2/1992 | Takayama et al. | |
| 5,096,671 A | 3/1992 | Kane et al. | |
| 5,114,864 A | 5/1992 | Walt | |
| 5,252,494 A | 10/1993 | Walt | |

(Continued)

FOREIGN PATENT DOCUMENTS

DE 34 40 177 5/1986

(Continued)

OTHER PUBLICATIONS

"Robots for the Future"—Shin-ichi, et al., Nov. 29, 2001.

(Continued)

*Primary Examiner* — Max Hindenburg
*Assistant Examiner* — Jonathan M Foreman
(74) *Attorney, Agent, or Firm* — Pearl Cohen Zedek Latzer, LLP

(57) ABSTRACT

Provided are a system and method for in vivo and in situ detection of body lumen conditions. The system comprises at least one interaction chamber for containing an endo-luminal sample, the interaction chamber comprising at least one indicator; at least one light source for illuminating the interaction chamber; and at least one optical detector for detecting in vivo optical changes occurring in the interaction chamber. The reaction between the indicator and sample may result in an optical change, which is detected and possibly imaged by the optical detector.

17 Claims, 3 Drawing Sheets

U.S. PATENT DOCUMENTS

| | | | |
|---|---|---|---|
| 5,279,607 A | 1/1994 | Schentag et al. |
| 5,368,027 A | 11/1994 | Lubbers et al. |
| 5,376,336 A | 12/1994 | Lubbers et al. |
| 5,395,366 A | 3/1995 | D'Andrea et al. |
| 5,582,170 A | 12/1996 | Soller |
| 5,604,531 A | 2/1997 | Iddan et al. |
| 5,697,384 A | 12/1997 | Miyawaki et al. |
| 5,762,770 A | 6/1998 | Pritchard et al. |
| 5,819,736 A | 10/1998 | Avny et al. |
| 5,833,603 A | 11/1998 | Kovacs et al. |
| 5,853,005 A | 12/1998 | Scanlon |
| 5,892,144 A | 4/1999 | Meller et al. |
| 5,932,480 A | 8/1999 | Maruo et al. |
| 5,993,378 A | 11/1999 | Lemelson |
| 6,006,121 A | 12/1999 | Vantrappen et al. |
| 6,074,349 A | 6/2000 | Crowley |
| 6,115,061 A | 9/2000 | Lieberman et al. |
| 6,165,128 A | 12/2000 | Cespedes et al. |
| 6,240,312 B1 | 5/2001 | Alfano et al. |
| 6,256,522 B1 | 7/2001 | Schultz |
| 6,330,464 B1 | 12/2001 | Colvin et al. |
| 6,330,465 B1 | 12/2001 | Huyberechts et al. |
| 6,498,941 B1 | 12/2002 | Jackson |
| 2001/0031502 A1 | 10/2001 | Watson, Jr. et al. |
| 2001/0034025 A1 | 10/2001 | Modlin et al. |
| 2001/0051766 A1 | 12/2001 | Gazdzinski |
| 2001/0053535 A1 | 12/2001 | Bashir et al. |
| 2002/0015952 A1 | 2/2002 | Anderson et al. |
| 2002/0103417 A1 | 8/2002 | Gazdzinski |
| 2003/0139661 A1 | 7/2003 | Kimchy et al. |
| 2003/0167000 A1 | 9/2003 | Mullick et al. |
| 2003/0208107 A1 | 11/2003 | Refael |

FOREIGN PATENT DOCUMENTS

| | | |
|---|---|---|
| EP | 0 693 271 | 1/1996 |
| EP | 0 945 102 | 9/1999 |
| JP | 57-45833 | 3/1982 |
| JP | 1107737 | 4/1989 |
| JP | 3-289779 | 12/1991 |
| JP | 4-109927 | 4/1992 |
| JP | 4109927 | 4/1992 |
| JP | 4-180736 | 6/1992 |
| JP | 6063051 | 8/1992 |
| JP | 5015515 | 1/1993 |
| JP | 5200015 | 8/1993 |
| JP | 2000506410 | 9/1998 |
| JP | 2001224553 | 2/2000 |
| WO | WO 92/21307 | 12/1992 |
| WO | WO 97/33513 | 9/1997 |
| WO | WO 98/11816 | 3/1998 |
| WO | WO 99/11754 | 3/1999 |
| WO | WO 00/13003 | 3/2000 |
| WO | WO 00/22975 | 4/2000 |
| WO | WO 01/07919 | 2/2001 |
| WO | WO 01/08548 | 2/2001 |
| WO | WO 01/25481 | 4/2001 |
| WO | WO 01/50941 | 7/2001 |
| WO | WO 01/53792 | 7/2001 |
| WO | WO 01/65995 | 9/2001 |

OTHER PUBLICATIONS

"Video Camera to "Take""—RF System lab., Dec. 25, 2001.
www.rfnorika.com—NORIKA3, Dec. 24, 2001.
The Radio Pill, Rowlands, et al., British Communications and Electronics, Aug. 1960, pp. 598-601.
Wellesley Company sends body monitors into space—Crum, 1998.
Wireless Transmission of a Color Television Moving Image from the Stomach using a Miniature CCD Camera, Light Source and Microwave Transmitter. Swain CP, Gong F, Mills TN. Gastrointest Endosc 1997; 45:AB40.
BBC News Online—Pill Camera to 'Broadcast from the Gut', Feb. 21, 2000, www.news.bbc.co.uk.
High Throughput Microchannel DNA Sequencer, Mar. 15, 2000.
What is Proteomics, Mar. 15, 2000.
www.cartesian.com—Nanoliter Quantitative Aspiration and Dispense (nQUAD) Technology, Mar. 15, 2000.
www.cartesiantech.com—Products for DNA Microarray Applications, Mar. 15, 2000.
www.cartesiantech.com—Synchronized nQUAD Technology, Mar. 15, 2000.
www.mbt.washington.edu—Leroy Hood, Research Focus, Mar. 15, 2000.
Merriam-Webster's Collegiate Dictionary, 2001, Merriam-Webster Incorporated. $10^{th}$ ed, 103.

SYSTEM AND METHOD FOR DETERMINING IN VIVO BODY LUMEN CONDITIONS

This application is a divisional of U.S. patent application Ser. No. 10/046,540, filed Jan. 16, 2002, now U.S. Pat. No. 7,468,044, which claimed the benefit of U.S. Provisional Patent Application No. 60/261,189, filed on Jan. 16, 2001, both of which are incorporated in their entirety by reference herein.

FIELD OF THE INVENTION

The present invention relates to the field of in vivo diagnostics. More specifically, the present invention relates to a system and method for the in vivo and in-situ detection of chemical and/or biological substances and for the in vivo detection of physical conditions in body lumens.

BACKGROUND OF THE INVENTION

An atypical concentration or presence of substances in body fluids or in body lumens is indicative of the biological condition of the body. For example, the presence of elevated concentrations of red blood cells in the gastrointestinal (GI) tract indicates different pathologies, depending on the location of the bleeding along the GI tract. Likewise, abnormalities in the physical conditions of the body, such as elevated temperature, may indicate a pathology. Early detection, identification and location of abnormal conditions are critical for correctly diagnosing and treating various pathologies.

Medical detection kits are usually based on in vitro testing of body fluid samples for the presence of a suspected substance. This method of detection does not easily enable the localization or identification of the origin of an abnormally occurring substance. In many instances localizing an abnormally occurring substance in a body lumen greatly contributes to the identification of a pathology, and thus contributes to the facile treatment of the identified pathology. For example, bleeding in the stomach may indicate an ulcer while bleeding in the small intestine may indicate the presence of a tumor.

The detection of bleeding in the GI tract is possible by endoscope, however this possibility is limited to the upper or lower gastrointestinal tract. Thus, bleeding in other parts of the GI tract, such as the small intestine, is not easily detected by endoscopy. Further, the commonly used diagnostic kits and methods for detecting blood in the GI tract do not enable the identification of the origin of the bleeding and further testing must be carried out to determine the type of pathology.

SUMMARY OF THE INVENTION

The present invention provides a system and method for in vivo and in situ detection of in vivo conditions.

The term "body lumen conditions" referred to herein relates to the presence and/or concentration of substances in body lumens and/or to physical conditions prevailing in the body lumen, such as, but not limited to, temperature, pressure or electric field.

Substances may be, inter alia, ions, molecules, cells, compounds such as proteins, sugars and blood components.

The system according to an embodiment of the invention includes at least one interaction chamber, at least one light source and at least one optical detector. According to an embodiment of the invention, the interaction chamber can contain an in vivo (endo-luminal) sample and contains at least one indicator such that the indicator can react with the sample. The endo-luminal sample has prevailing conditions or possibly contains a substance such that the indicator contained within the interaction chamber reacts to the prevailing conditions or reacts with the substance, the reaction resulting in an optical change occurring in the interaction chamber.

The light source illuminates the interaction chamber, which is transparent in the wavelength of light that illuminates it, and the optical detector detects in vivo optical changes possibly occurring in the interaction chamber.

According to an embodiment of the invention, the system is inserted into a body lumen and a sample from the body lumen environment is drawn into an interaction chamber which comprises at least one indicator. The interaction chamber is preferably designed such that it is permeable to the body lumen fluids and substances, allowing them to enter the chamber but not enabling leakage of the indicator from the chamber into the body lumen environment.

The indicator may be contained as a liquid or suspension within selective membranes in the interaction chamber, which allow the passage of body lumen fluids but do not allow the passage of the indicator. Alternatively, the indicator may be immobilized onto the interaction chamber walls or onto an appendage that is restricted to the interaction chamber such that the indicator cannot leave the interaction chamber. Other configurations of an interaction chamber comprising an indicator are possible.

A reaction between the sample and indicator may result in an optical change, such as, but not limited to, a change of color or a change in the optical density in the interaction chamber. These optical changes are detected and possibly imaged by the optical detector. The detected image, which may contain diagnostic information, may be stored to be retrieved at a later time or may be transmitted to an external receiver.

The system, according to an embodiment of the invention, may utilize an imaging and transmitting system such as that utilized with the swallowable capsule described in U.S. Pat. No. 5,604,531 or that described in WO 01/65995. U.S. Pat. No. 5,604,531 and WO 01/65995, which are assigned to the common assignee of the present application, are hereby incorporated by reference.

According to an embodiment of the invention, the interaction chamber contains indicators capable of reacting to physical conditions such as temperature or capable of reacting with specific chemical or biological substances that may be present in the body lumen fluids. The reaction results in an optical change. The optical change may be qualitative, merely detecting and indicating the presence of the substance in the body lumen environment, and/or quantitative, showing the concentration of the substance in the body lumen environment.

The method according to an embodiment of the invention comprises the steps of inserting into a body lumen the system according to an embodiment of the invention, receiving an endo-luminal sample in the interaction chamber, such that the endo-luminal sample and/or a substance possibly contained within the endo-luminal sample, can react with the indicator, illuminating the interaction chamber and detecting optical changes occurring in the interaction chamber.

According to an embodiment of the invention, the system of the invention can be inserted into body lumens when it is attached to or contained within a device designed for being inserted into body lumens, such as needles, stents, endoscopes or swalloable capsules.

In one embodiment of the invention, the optical detector is an imager, such as a CCD, photodiodes or a CMOS imaging chip. In one embodiment the optical change can be imaged.

In yet another embodiment the system can detect body lumen conditions in-situ. According to one embodiment the optical detector is an imager that images both the body lumen and the optical changes occurring in the interaction chambers. Imaging the body lumen supplies information regarding the location of the system in the body lumen (for example as described in the above mentioned U.S. Pat. No. 5,604,531) at any given time, such that the occurrence of an optical change can be localized to a specific site in the body lumen and pathologies can be identified and localized to a certain area in the body lumen.

In another embodiment of the invention the system is contained within a device that is capable of autonomously imaging and sampling the entire GI tract, such as a swallowable capsule.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Figure 1:
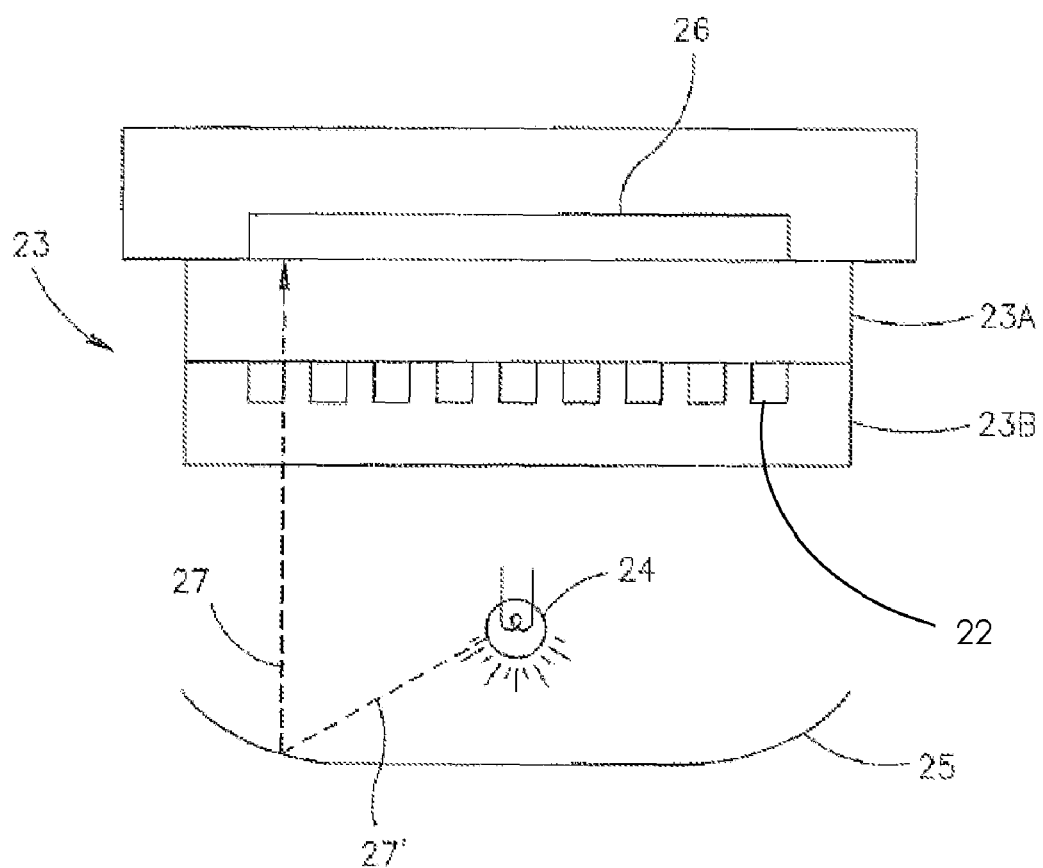
FIG. 1 is a schematic side view illustration of the system according to an embodiment of the invention.

Reference is now made to FIG. 1 in which an embodiment of the system of the invention is schematically illustrated. The system comprises interaction chambers 22, a light source 24 which illuminates the interaction chambers 22 and an optical detector 26 for detecting optical changes in the interaction chambers 22, for example by imaging the interaction chambers 22. The interaction chambers 22 contain indicators (not shown) that can react to physical conditions or react with substances to give an optically detectable result, such as a change of color or a change in optical density.

When the system is introduced into a body lumen the lumen environment is sampled. An endo-luminal sample may be passively drawn into the interaction chamber for example, by the capillary action of the interaction chamber, or the sample may be actively drawn, for example by using any suitable mechanical micro pump known in the art, such as an osmotic pump (available in silicon). Alternatively, the sampling can be periodic, controlled, for example, by a switch.

The interaction chambers 22 may each comprise two openings to allow discharge and replacement of the sample in the chamber as the system samples new areas of the body lumen environment.

The interaction chambers 22, which are configured for containing endo-luminal samples, such as body lumen fluids, comprise an indicator or combination of indicators, such that a reaction between the indicators and the sample or substances possibly contained in the sample may occur in the interaction chambers 22.

The interaction chambers 22 are illuminated by light source 24 such that optical changes that occur in them may be detected by optical detector 26. These optical changes are a result of the physical conditions prevailing in the sample and their effect on the indicator or of the interaction between the indicator and a substance or substances contained in the sample. For detecting or imaging the optical changes, at least a portion of the interaction chambers 22 is preferably transparent in the wavelength of illumination.

The interaction chambers 22 may be formed as capillaries etched into a slab of glass 23, or formed in between two glass slabs 23A and 23B one of which (23B) contains preformed slots or channels.

It will be appreciated that the interaction chambers may be made of any suitable material such as plastic, glass etc. Parameters to be considered while assessing if a material is suitable may be, for example, the material's transparency, its safety for internal use, its durability under endo-luminal conditions or under erosion inflicted by the interaction that may take place within it, and so on.

The system may comprise one or more interaction chambers such that one or more physical conditions or the presence and/or concentration of one or more substances may be detected simultaneously.

The indicators contained within the interaction chambers 22 may be reactive chemical components, biologically active agents such as enzymes or cells, immunoreagents or any indicator or mixture of indicators suitable for reacting to physical conditions or for reacting with substances.

In accordance with specific reaction requirements and specific indicator/substance properties, the indicators may be contained in the interaction chamber in solution or in solid form such as an indicator layer coating the interaction chamber walls or as an indicator immobilized onto an appendage that is restricted to the interaction chamber. For example, an indicator coated strip may be anchored to the interaction chamber wall or indicator coated beads may be entrapped in the interaction chamber. For example, orthotolidine may be impregnated on the interaction chamber walls or on a strip anchored to the interaction chamber. Erythrocytes (red blood cells) present in the body lumen environment entering the interaction chamber can be hemolyzed liberating free hemoglobin, which catalyzes orthotolidine oxidation, producing a blue color. The intensity of the color change is proportional to the amount of blood in a body lumen fluid. Other indicators may be used such as pH indicators, indicators of sugar, antibodies having an affinity to specific substances or cells etc. It will be appreciated that the system of the invention can also be used for detecting different physical conditions of the body lumen and its environment. Thus, for example, temperature changes in different areas of a body lumen may be detected by using an indicator that changes color in accordance with the sensed temperature.

The reaction between the indicator and a substance may be reversible, in which case the indicator can be used to detect a plurality of substance sources, each source showing as a single event of optical change. Also, the reaction kinetics may be such that the intensity of the optical change is proportional to the substance concentration, thus enabling to deduce the substance concentration.

The interaction chambers 22 are illuminated by light source 24 which may be any illumination source compatible with the interaction chamber 22 and optical detector 26. Light sources such as light emitting diodes (LEDs) can be used. Optionally, a collimator or reflector 25 may be used for collecting/directing light rays from the light source 24 to the interaction chambers 22 and through them to the optical detector 26.

The optical detector 26 may be any device suitable for receiving and processing light rays that have passed through the interaction chambers 22.

The system my be set up such that the interaction chambers 22 are positioned in between a light source 24 on one side and an optical detector 26 on the other. Light rays (represented by arrow 27') emitted from the light source 24 are collected by collimator or reflector 25 and are directed (represented by arrow 27) at the glass slab 23 containing the interaction chambers 22. The light rays (represented by arrow 27) pass through the glass slab 23 and interaction chambers 22 and are received by the optical detector 26. The optical detector 26 may be any detector suitable for detecting optical changes, for example an imager, such as a CCD, CMOS imaging chip, photodiodes etc.

The optical detector 26 processes the received light rays for example by forming an image of the interaction chambers. The image may be stored in the optical detector 26 or may be further transmitted to an external receiving system.

The components of the system of the invention may be specifically designed for the system, or the system may utilize some components from other systems that operate in body lumens, thus economically taking advantage of existing components. For example, the system of the invention may be incorporated into or affixed onto medical devices meant for being inserted into body lumens, such as needles, stents, endoscopes or capsules that can pass through the GI tract. Endoscopes utilize a light source and sometimes an imaging device while operating. Thus, the system of the invention can be incorporated into an endoscope and utilize the endoscope's light source and imaging device for detecting the presence and/or concentration of substances or for measuring physical conditions of body lumens.

Figure 2:
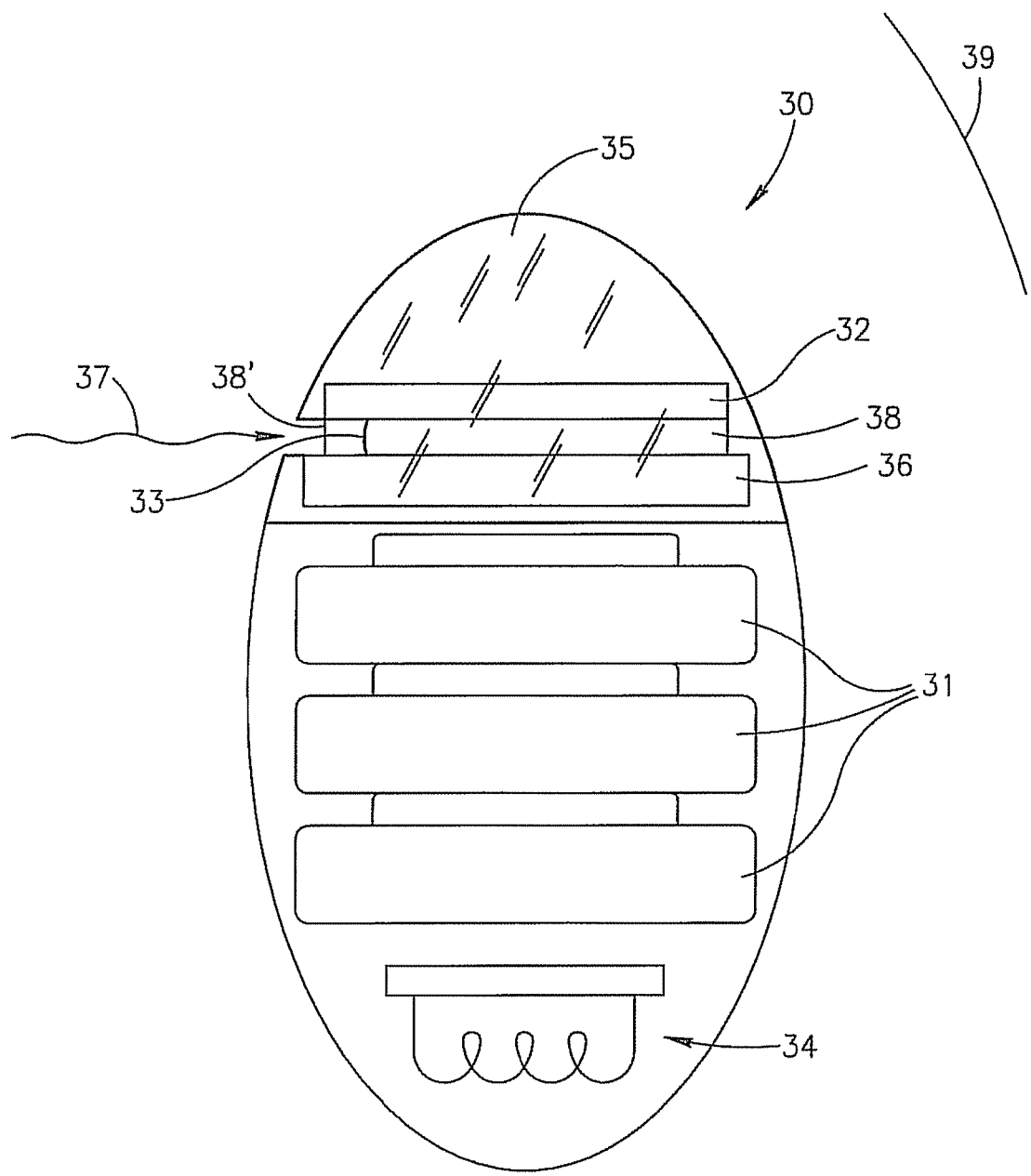
FIG. 2 is a schematic illustration of a capsule comprising the system according to an embodiment of the invention.

Reference is now made to FIG. 2, which schematically illustrates a device comprising the system, according to an embodiment of the invention. The device is capable of being inserted into and passing through body lumens, such as the GI tract and blood vessels, similarly to capsules known in the art.

For example, the swallowable capsule described in U.S. Pat. No. 5,604,531 can pass through the entire digestive tract and thus can operate as an autonomous video endoscope. A capsule optionally utilized according to an embodiment of the invention may include an imaging system, such as a video camera system and a transmitter, optionally a wireless transmitter, which transmits the video output of the imaging system. The exact location of the capsule can be known at any given time enabling to associate a specific image with a specific location of the capsule in the GI tract. Other capsules are described in U.S. Pat. No. 6,240,312, To Alfano, and in WO01/50941 to Refael, both of which are incorporated herein by reference. A capsule optionally utilized according to another embodiment of the invention may be a remote-controllable, micro-scale device having a motion mechanism, such as a mechanical propeller that may be driven by an electric motor or may be turned by a build in gas flow. Another capsule may contain a rotation mechanism that can be charged by external radio waves and that can initiate capsule rotation.

Referring now to FIG. 2, device 30 comprises a planar light source 32, an imaging device 36, such as a CCD or CMOS imaging chip and an interaction chamber 38 all positioned behind an optical window 35. Device 30 further comprises a battery 31 for supplying power to the elements of the device and a transmitter 34 for transmitting signals from the imaging device 36 to an external receiving system (not shown). In another embodiment device 30 may utilize an LED, such as white LEDs, to illuminate the interaction chambers 38. In yet another embodiment the device 30 may include an externally powered mechanism for providing power to the elements of the device. Also, the imaging device 36 may include an optical system, for example an array of microlenses and focusing elements. In an embodiment of the invention the device may comprise a plurality of imaging devices and, optionally, their corresponding optical systems, and optionally a plurality of illumination sources. For example, a plurality of imaging devices and optionally a plurality of interaction chambers may be positioned at opposing sides of the device for multi-directional sampling and/or viewing of the body lumen.

Device 30 will be demonstrated as a capsule capable of passing through and sampling the GI tract, however, other devices capable of passing through and sampling other body lumens are also possible according to embodiments of the invention.

Once device 30 is inserted into the GI tract, for example by swallowing, and the imaging device 36 and light source 32 are operated, the GI tract walls 39 and the interaction chamber 38 are directly illuminated by light source 32 and imaged by imaging device 36. The images are transmitted to an external receiving system, for example, as described in U.S. Pat. No. 5,604,531.

The interaction chamber 38 is open to the GI tract environment, such that GI tract fluids 37 can enter the interaction chamber 38 through opening 38', either passively or actively as described above. The indicators (not shown) contained within the interaction chamber are restricted to the interaction chamber. The indicators may be immobilized as described above or they may be unable to leave the interaction chamber because of selective barriers in the interaction chambers as demonstrated in FIG. 2 and as described below.

In the embodiment illustrated in FIG. 2 the interaction chamber 38 comprises a selective membrane 33, which enables the entrance of GI tract fluids 37 but does not allow leakage of the indicators from the interaction chamber 38.

As the device 30 proceeds down the GI tract, minute amounts of GI tract fluids 37 slowly enter the interaction chambers 38 and the entire GI tract can be sampled into a single interaction chamber. Alternatively, the system may be configured such that GI tract fluids that have entered the interaction chamber in one area of the GI tract are displaced by fluids from a newly reached area in the GI tract. In this case the interaction chambers would have two openings and two membranes for restricting the indicator to the interaction chamber.

Device 30 constantly samples the GI tract environment throughout the lumen. Thus, the origin or exact location of pathologies in the GI tract can be detected. For example, the origin of bleeding in the GI tract can be detected as follows. A patient has device 30 inserted into his GI tract. The device comprises an imager and at least one interaction chamber comprising an indicator of blood or of blood components. The device passively travels through the patient's GI tract imaging both the GI tract and the interaction chamber. In a location of bleeding in the GI tract, the sampled GI tract fluids will contain blood. The blood will react with the indicator in the interaction chamber 38 resulting in an optical change that will be imaged by the optical detector 36. The image of the optical change and of the location in the GI tract will be transmitted to an external operator who can identify the location of the device 30 at the time the image was produced and thus identify the origin of bleeding. Several origins of bleeding along the GI tract can be identified and the intensity of bleeding at each origin can be determined judging by the concentration of blood at each location.

Device 30 schematically shown in FIG. 2 is designed to be inserted into the GI tract and pass through the entire tract, similarly to the capsule described in U.S. Pat. No. 5,604,531. However, as mentioned above, device 30 is not limited to any specific configuration. Rather, the device may be of any shape suitable for being inserted into a body lumen and for passing through the body lumen or for being included in a device that is inserted into a body lumen. Further, in accordance with the specific imager and specific energy requirements, device elements (such as the illumination source and transmitter) may be connected by cable to an external power supply or to an external receiving system.

Figure 3:
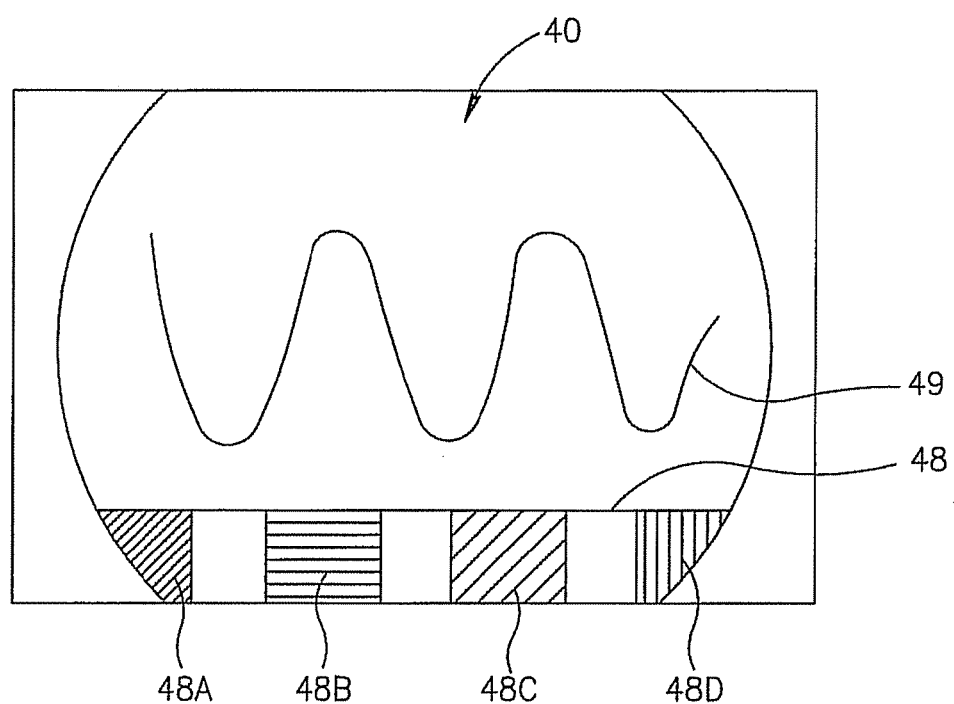
FIG. 3 is a schematic illustration of the picture field obtained by the system according to an embodiment of the invention.

Reference is now made to FIG. 3, which schematically shows the picture field obtained by an imager in device 30. According to an embodiment of the invention a single imaging device (36 in FIG. 2) is used for the imaging of both the GI tract walls and the interaction chambers. Thus, the picture field 40 obtained from the imaging device contains both images of the GI tract wall 49 and images of the interaction chambers 48. Different interaction chambers 48A-D may contain different indicators such that the pattern of colors or other optical changes appearing in image 48, in picture field 40, corresponds to the different endo-luminal substances in the GI tract.

It will be appreciated that a picture field may be obtained from different images obtained from a plurality of different imaging devices or optical detectors which are combined, for convenience, into one picture field similar to picture field 40.

Thus, by using the system of the invention it is possible to obtain a "profile" of substances or physical conditions for any location in a body lumen. The "profile" deduced from image 48 together with the data derived from the image of the GI tract wall 49, can be used in in vivo diagnostics, such as diagnostics of the GI tract.

It will be appreciated by persons skilled in the art that the present invention is not limited to what has been particularly shown and described hereinabove. Rather the scope of the present invention is defined only by the claims which follow:

The invention claimed is:

1. An in-vivo imaging device for determining an in vivo condition, the imaging device comprising:
   an illumination source;
   an interaction chamber comprising first and second openings, wherein the first opening allows an endo-luminal sample to enter and the second opening allows discharge of the endo-luminal sample; and
   an optical detector for capturing an image of at least the interaction chamber,
   wherein the optical detector is positioned on the opposite side of the interaction chamber from said illumination source, and
   wherein the interaction chamber and the optical detector are positioned behind an optical window.

2. The in-vivo imaging device according to claim 1 wherein the interaction chamber includes a capillary.

3. The in-vivo imaging device according to claim 1 wherein the interaction chamber is etched into a slab of glass.

4. The in-vivo imaging device according to claim 1 wherein the interaction chamber includes an indicator configured to react with the endo-luminal sample.

5. The in-vivo imaging device according to claim 4, comprising first and second membranes configured to restrict the indicator to the interaction chamber.

6. The device according to claim 4,
   wherein said interaction chamber comprises a first interaction chamber and said indicator comprises a first indicator;
   wherein said device further comprises a second interaction chamber comprising a second indicator configured to react with at least the endo-luminal sample, and
   wherein each of said first and second interaction chambers comprises first and second openings, wherein each first opening allows an endo-luminal sample to enter the respective chamber and each second opening allows discharge of the endo-luminal sample from the respective chamber.

7. The in-vivo imaging device according to claim 1, comprising first and second membranes configured to selectively enable passage of the endo-luminal sample.

8. The in-vivo imaging device according to claim 1, comprising an optical system.

9. The in-vivo imaging device according to claim 1 comprising a transmitter to transmit the captured image to an external receiving system.

10. The in-vivo imaging device according to claim 1, wherein the optical detector is configured for capturing an image of the interaction chamber and a gastrointestinal tract wall.

11. An in-vivo imaging device for determining body lumen conditions in-vivo, the in-vivo device comprising:
    an illumination source, an interaction chamber, an optical detector and an optical window,
    wherein said interaction chamber and said imager are positioned within said imaging device behind said optical window, said optical detector is positioned on the opposite side of the interaction chamber from said illumination source, and said optical detector captures images of said interaction chamber;
    a first opening of the in-vivo interaction chamber through which an endo-luminal sample may enter, the interaction chamber having immobilized therein an indicator configured to react with at least the endo-luminal sample, said reaction occurring within the interaction chamber, and the reaction resulting in an optical change; and
    a second opening of the interaction chamber through which the endo-luminal sample may be discharged.

12. The device according to claim 11, wherein said optical detector captures an image of a gastrointestinal wall.

13. The device according to claim 11, wherein said optical detector captures images of said body lumen in addition to said interaction chamber.

14. The device according to claim 11, wherein said optical detector captures images of optical changes that occur within the interaction chamber.

15. The device according to claim 11, further comprising an illumination source to illuminate said interaction chamber wherein at least a portion of the interaction chamber is transparent in a wavelength of illumination.

16. The device according to claim 11, further comprising a transmitter to transmit images to an external receiver.

17. The device according to claim 11,
    wherein said interaction chamber comprises a first interaction chamber and said indicator comprises a first indicator;
    wherein said device further comprises:
       a second interaction chamber comprising a second indicator configured to react with at least the endo-luminal sample,
       a first opening in the second in-vivo interaction chamber through which an endo-luminal sample may enter, and
       a second opening in the second in-vivo interaction chamber through which the endo-luminal sample may be discharged.

* * * * *